US008855736B2

(12) United States Patent  (10) Patent No.: US 8,855,736 B2
Jaffe et al.  (45) Date of Patent: Oct. 7, 2014

(54) SAFETY TRANSCUTANEOUS ELECTRODE

(76) Inventors: Richard A. Jaffe, Stanford, CA (US);
Jaime R. Lopez, El Granada, CA (US);
Alan Chris Allison, Brentwood, CA (US)

( * ) Notice: Subject to any disclaimer, the term of this patent is extended or adjusted under 35 U.S.C. 154(b) by 125 days.

(21) Appl. No.: 13/198,005

(22) Filed: Aug. 4, 2011

(65) Prior Publication Data

US 2012/0035451 A1   Feb. 9, 2012

Related U.S. Application Data

(60) Provisional application No. 61/371,050, filed on Aug. 5, 2010.

(51) Int. Cl.
*A61B 5/04* (2006.01)
*A61B 5/0492* (2006.01)
*A61B 5/0408* (2006.01)
*A61B 5/0478* (2006.01)
*A61F 7/12* (2006.01)
*A61N 1/00* (2006.01)
*A61B 5/042* (2006.01)
*A61B 5/00* (2006.01)
*A61M 5/32* (2006.01)

(52) U.S. Cl.
CPC .............. *A61B 5/0408* (2013.01); *A61B 5/042* (2013.01); *A61B 5/0492* (2013.01); *A61B 5/6801* (2013.01); *A61M 5/3273* (2013.01); *A61B 5/0478* (2013.01); *A61B 5/04001* (2013.01); *A61B 2562/18* (2013.01); *A61B 2562/14* (2013.01); *A61B 5/6839* (2013.01)
USPC ........................... 600/372; 604/113; 607/115

(58) Field of Classification Search
CPC .. A61B 5/0492; A61B 5/6848; A61B 5/6849; A61B 5/685
USPC .......................................... 600/372–373, 376
See application file for complete search history.

(56) References Cited

U.S. PATENT DOCUMENTS

| | | | | |
|---|---|---|---|---|
| 4,151,835 A | * | 5/1979 | Showell et al. | 600/376 |
| 4,294,258 A | * | 10/1981 | Bernard | 600/351 |
| 7,310,546 B2 | * | 12/2007 | Prass | 600/373 |
| 2002/0055711 A1 | * | 5/2002 | Lavi et al. | 604/110 |
| 2004/0147996 A1 | * | 7/2004 | Miazga et al. | 607/142 |
| 2008/0009763 A1 | * | 1/2008 | Chiou et al. | 600/544 |

* cited by examiner

*Primary Examiner* — Linda Dvorak
*Assistant Examiner* — Brian M Antiskay
(74) *Attorney, Agent, or Firm* — Leighton K. Chong

(57) ABSTRACT

Transcutaneous safety electrode assemblies are described that can include a conducting electrode having a sharp end to penetration of the skin of a patient, and a shielding member that is deployable by a user so as to shield the sharp end of the electrode after the electrode is removed from the skin. The shielding member can be deployed by retracting the sharp end of the electrode a protective housing, assisted by spring force provided by the electrode wire so as to self-retract into the protective housing. The deployment and disengagement can be via push button action, and the electrode assembly can be self-retaining on the patient's skin while deployed.

14 Claims, 16 Drawing Sheets

SAFETY TRANSCUTANEOUS ELECTRODE

CROSS-REFERENCE To RELATED APPLICATION

This patent application claims the benefit of U.S. Prov. Ser. No. 61/371,050 filed Aug. 5, 2010, which is incorporated by reference herein.

BACKGROUND

When making measurements of electrical activity in the human body, such as for Electroencephalography (EEG), Electrocardiography (ECG), Electromyography (EMG), Evoked Potentials (EPs), Electronystagmography (ENG), and/or other electrophysiologic potentials, there are several types of electrodes that are commonly used. Surface electrodes can be attached to the surface of the patient's skin using adhesives such as glue or using tape or staples. In order to make good electrical contact, a conductive gel or paste is often used between the electrode and the skin. Surface electrodes, however suffer from a number of disadvantages. The conductive gel used can, over time, dry out or otherwise degrade so as to change the effective impedance value. This is especially true during long procedures such as a surgery lasting as long as six hours or more. Surface electrodes can also dislodge, when glue and/or tape is used. If staples are used then there is an associated tissue injury, pain, and risk of infection. Some glue adhesives are flammable and may be incompatible with application in an operating room. In some cases, such as when placing electrodes on skin with hair or on the scalp, an abrasion is made to remove dead skin cells and reduce impedance. However, such abrasion can cause further discomfort to the patient as well as add time to the process.

Subdermal electrodes, such as needle electrodes are sometimes used, to alleviate some of the drawbacks associated with surface electrodes. In particular, subdermal needle electrodes avoid the use of adhesive glues, abrasions prior to placement, and the use of conductive gels or pastes that can raise impedance over time. Needle electrodes can also be easier to place, thereby lessening the time needed to set up the procedure. However needle type subdermal electrodes have drawbacks as well. A primary concern is for the safety of the medical personnel, such as doctors, nurses, technologist, and other personnel that can be inadvertently injured by the needle electrode after it is removed from the patient. These sharps injuries expose the personnel to bloodborne pathogens that are present in human blood and can cause disease in humans. Examples of such pathogens includes Human Immunodeficiency Virus (HIV), Hepatitis B Virus (HBV), and Hepatitis C Virus (HCV). Other drawbacks of needle type subdermal electrodes include stabilization of the electrode when positioned on the patient. Needle electrodes can be taped in place but tape is typically insufficient to secure the electrode. Staples can be used, but they present an additional sharps hazard and associated infection risk.

SUMMARY

According to some embodiments, a transcutaneous safety electrode assembly is provided that includes a conducting electrode member having a sharp portion dimensioned for penetration of the skin surface of a patient, and a shielding member that is deployable by a user so as to shield the sharp portion of the electrode member after the electrode member is removed from the skin.

According to some embodiments, an insulated elongated electrically conducting member is provided that is in electrical communication with the electrode member. According to some embodiments, the electrode is used transcutaneously. According to some embodiments, the electrode is used intramuscularly.

According to some embodiments the shielding member is deployed by retracting at least the sharp portion of the electrode member into a protective housing According to some embodiments, the sharp portion is retracted in to the protective housing at least partially assisted by a spring force so as to at least partially self-retract into the protective housing. The spring force can be provided at least in part by the conducting electrode member.

According to some embodiments wherein the electrode member is curved and can be deployed in the skin using a screwing action.

According to some embodiments, the electrode member is deployed by the user pressing a button.

According to some embodiments the electrode assembly includes a second sharp portion.

According to some embodiments the electrode assembly remains retained on the skin of the patient when the sharp portions are penetrating the skin of the patient.

According to some embodiments the electrode assembly includes two or more electrodes so as to provide a bi-polar electrode functionality.

It will be appreciated that these systems and methods are novel, as are applications thereof and many of the components, systems, and methods employed therein. It should be appreciated that embodiments of the presently described inventive body of work can be implemented in numerous ways, including as processes, apparatuses, systems, devices, methods, and/or as a combination thereof. Several illustrative embodiments are described below.

BRIEF DESCRIPTION OF THE DRAWINGS

The inventive body of work will be readily understood by referring to the following detailed description in conjunction with the accompanying drawings, in which.

DETAILED DESCRIPTION

A detailed description of the inventive body of work is provided below. While several embodiments are described, it should be understood that the inventive body of work is not limited to any one embodiment, but instead encompasses numerous alternatives, modifications, and equivalents. In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body of work.

Figure 1A:
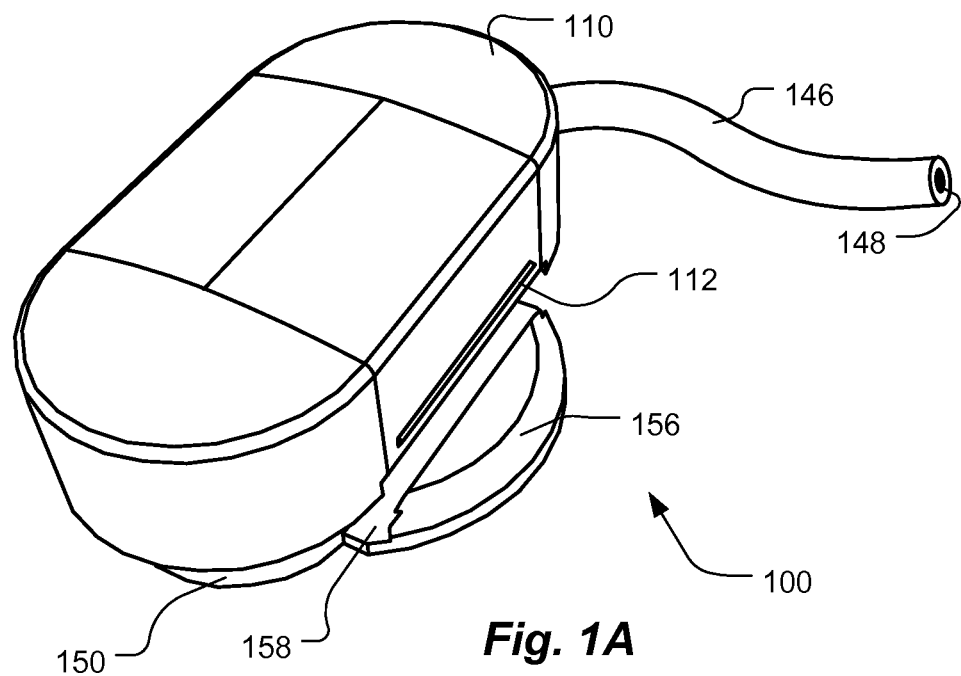
FIGS. 1A-D are perspective views of a safety transcutaneous electrode assembly, according to some embodiments.

FIGS. 1A-D are perspective views of a safety transcutaneous electrode assembly, according to some embodiments. In FIG. 1A, electrode assembly 100 is shown prior to installation or placement on the patient. Upper housing 110 is preferably made from injection molded ABS and includes two locking detent portions, one locking detent portion 112 is shown in FIG. 1A while the other is on the far side wall. The upper housing 110 has an upper surface that acts as a button to facilitate installation of the electrode assembly. The upper housing 110 fits over a lower housing 150 which is also preferably made of injection molded ABS. Lower housing 150 includes two notched portions, one of which, namely notched portion 158 is shown. Lower housing 150 also includes two release buttons, one of which, namely release button 156 is shown. Electrode wire 146 is also shown which is insulated and has a central conducting core 148 of wire or wires.

Figure 1B:
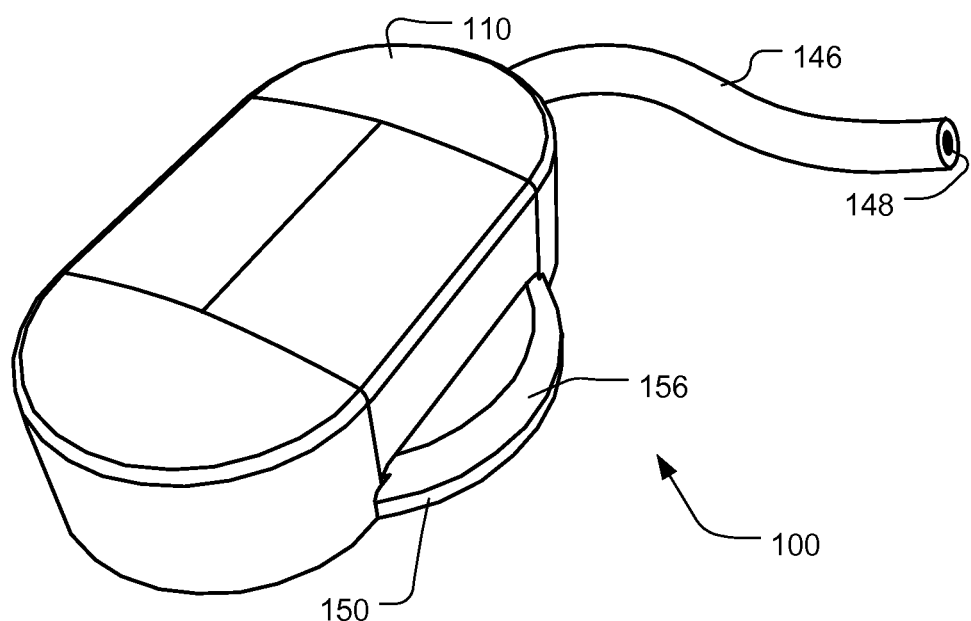

FIG. 1B shows electrode assembly 100 while installed in the tissue of a patient. Note that the upper housing 110 is pressed into lower housing 150 such that the side walls of upper housing 110 fit into the notched portions in the lower housing. Two electrode wires having sharp portions are pressed into the skin of the patient during installation. The upper housing 110 and lower housing 150 are held together by the locking detent portions engaging with matching detent portions on the lower housing 150. When the electrode is to be removed from the patient, the two release buttons are pressed so as distort the lower housing 150 and unmate the locking detent portions from each other. After the electrode is removed the sharp portions of the electrode wires are withdrawn back into the cavity formed by the upper and lower housings, such that the sharp portions of the electrode wires do not present a sharps hazard.

Figure 1C:
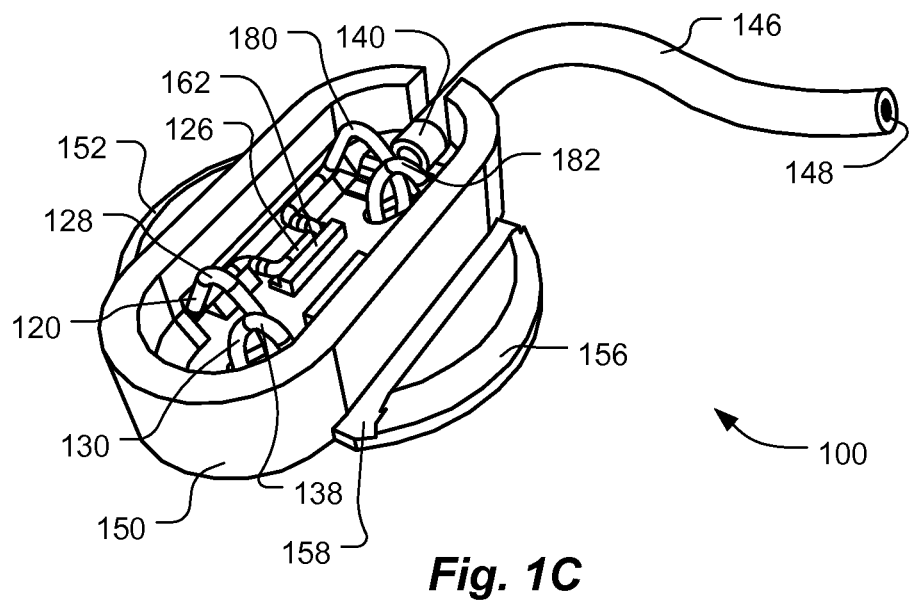

FIG. 1C shows the electrode assembly prior to installation with the upper housing removed for clarity of other portions of the electrode assembly. Two electrode wires 120 and 130 are shown. The electrode wires 120 and 130 are preferably made of titanium (e.g. grade 5 or 301 stainless steel) and can be of suitable gauge for the application. For scalp electrodes for use with EEG measurement and/or other brain electrical activity, a wire diameter is 0.015 inches is suitable. Wires 120 and 130 each include two sharp portions that during installation protrude through windows in the lower housing 150. Contact plate 140 includes contact pads for contact with wires 120 and 130. The conducting core 148 of electrode wire 146 is electrically connected to contact plate 140. Prior to installation and after removal from the patient, the electrode wire 120 has raised portions 128 and 180, and wire 130 has raised portions 138 and 182. Each wire also has a bent portion to provide torsional force. In particular, bent portion 126 can be seen on wire 120 which fits into slot formed by raised section 162 on lower housing 150. The raised portions are engaged by the upper housing 110 such that by pressing the upper housing 110 into the lower housing 150 upon installation, the raised portions 128, 138, 180 and 182 push the sharp portions of the electrode wires into the patient's skin. Upon installation a torsional force is also applied to the wires since the bent portion on each wire cannot move within the mating slot on the lower housing. In the case of wire 120, the bent portion 126 cannot move within the mating slot formed by raised section 162 on lower housing 150. Upon removal the torsional spring force from the wires act such that the raised portions push the upper housing 110 back up and away from the lower housing 150 and the sharp portions of the electrode wires are withdrawn from the patient's skin and back into the cavity between the upper and lower housing.

Figure 1D:
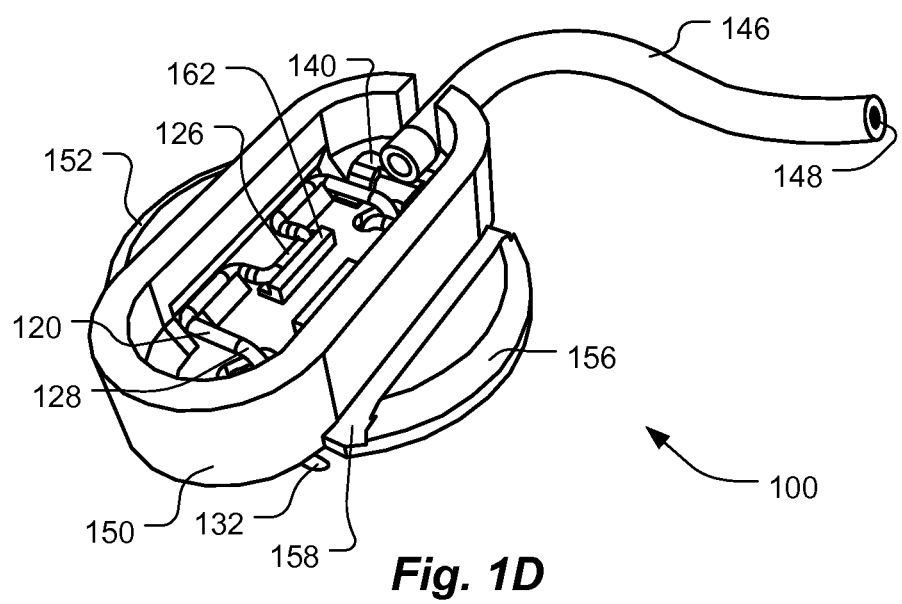

FIG. 1D shows the electrode assembly during installation in the skin of a patient. Note that the raised portions of wires 120 and 130 are pushed down flat onto the lower floor of lower housing 150. One of the sharp portions, sharp portion 132 of electrode wire 130 can be seen protruding below the bottom of the lower housing 150.

Figure 2:
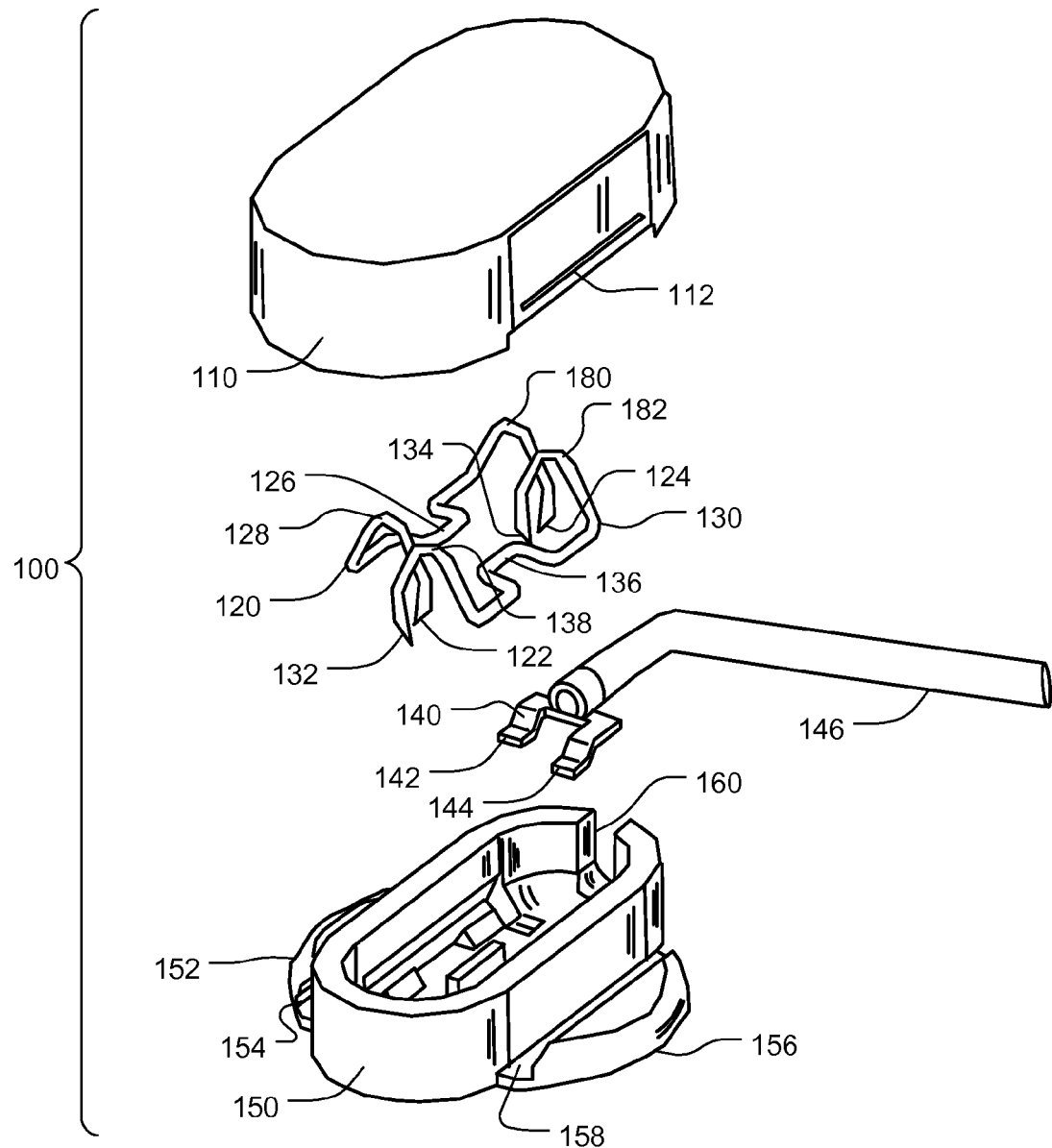
FIG. 2 is an exploded view of a safety transcutaneous electrode assembly, according to some embodiments.

FIG. 2 is an exploded view of a safety transcutaneous electrode assembly, according to some embodiments. Upper housing 110 is preferably made of injection molded ABS and includes a locking detent portion 112. Two electrode wires 120 and 130 are preferably made of titanium (e.g. grade 5 or 301SS) and can be of suitable gauge for the application. For scalp electrodes, a wire diameter is 0.015 inches is suitable. Wire 120 includes two sharp portions 122 and 124, two raised portions 128 and 180, and bent portion 126. Likewise, wire 130 includes two sharp portions 132 and 134, two raised portions 138 and 182, and bent portion 136. Contact plate 140 includes a contact pad 142 for contact with wire 120, and pad 144 for contacting with wire 130. The electrode wire 146 is connected to contact place 140 and is insulated. A lower housing 150 is preferably made of injection molded ABS. Lower housing 150 includes a notch 160 to accept the electrode wire 146. Two release buttons 152 and 156 are provided to release the electrode from the skin.

When assembled, the upper housing 110 acts as a push button to deploy the electrode assembly 100 on the patient's skin. Downward pressure from upper housing 110 pushes on the raised portions of wires 120 and 130 such that the sharp portions 122, 124, 132 and 134 are pushed through the surface of the patient's skin. When the upper housing 110 is fully pressed the detent portion on either side of the upper housing mate with detents on push buttons on the side of notched portions 154 and 158 thereby maintaining the extension of the wires 120 and 130 in patient's skin and retaining the electrode assembly in place on the patient.

When release buttons 152 and 156 are pressed by a user the mated detent portions on the upper and lower housings are disengaged and the torsional spring force from the wires 120 and 130 act to retract the sharp portions back into the lower housing 150, so as to significantly reduce or eliminate the risk of being injured by the sharp portions of the wires 120 and 130.

According to some embodiments, an electrode gel and/or germicidal capsule is provided inside the cavity between the upper and lower housings so as to further reduce impedance and/or reduce risk of infection.

According to some embodiments, the two wires 120 and 130 can be separately connected to respective insulated conductors so that impedance can be checked separately. According to some embodiments separate conductors are provided such that the electrode assembly is bipolar.

Figure 3A:
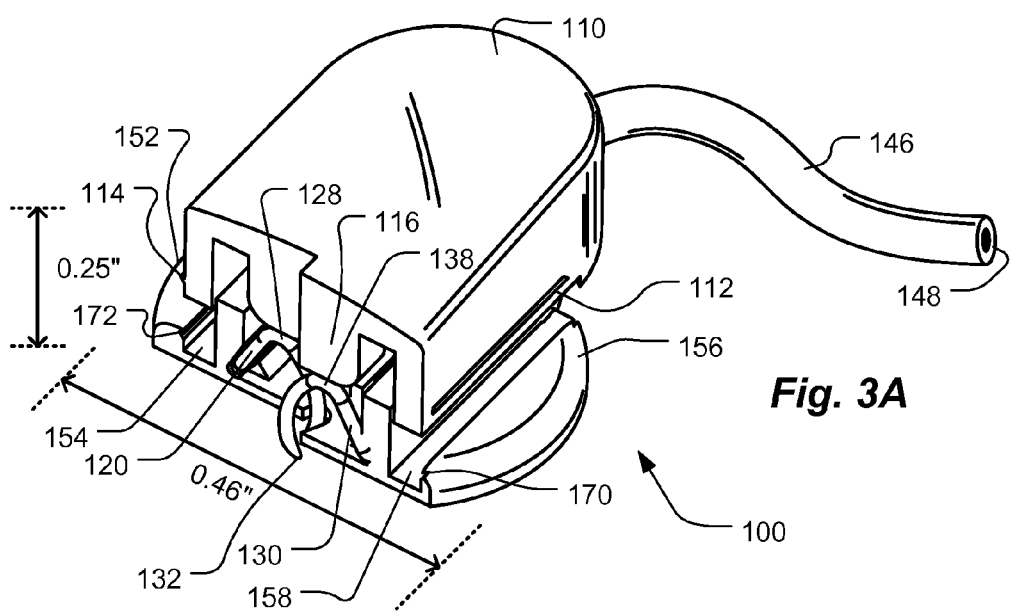
FIGS. 3A-B are cut-away perspective views of an electrode assembly, according to some embodiments.
Figure 3B:
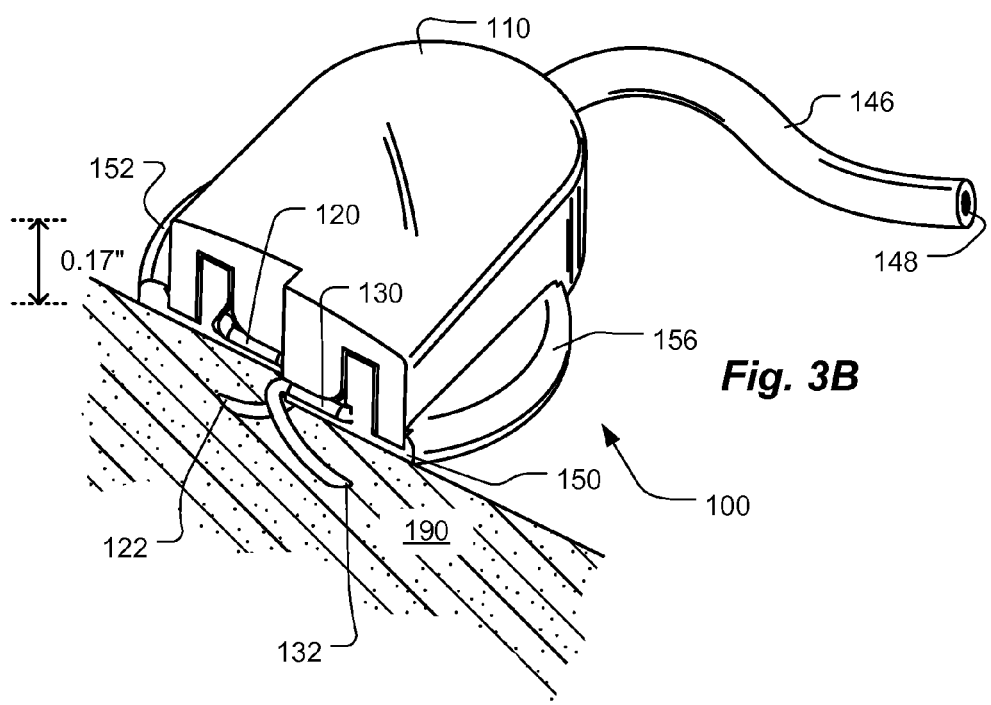

FIGS. 3A-B are cut-away perspective views of an electrode assembly, according to some embodiments. FIG. 3A shows a portion of electrode assembly 100 prior to installation on a patient's tissue. According to some embodiments, electrode assembly has an overall width of about 0.46 inches, and prior to installation, the electrode assembly has an overall height of about 0.25 inches. Upper housing 110 is shown having two locking detent portions 112 and 114. Two electrode wires 120 and 130 are shown, and in the case of wire 130, raised portion 138 and sharp portion 132 are shown. The conducting core 148 of electrode wire 146 is electrically connected to a contact plate that is electrical contact with the electrode wires 120 and 130. As can be seen, the raised portion 138 is engaged by protrusion 116 on the upper housing 110 such that by pressing the upper housing 110 into the lower housing 150 upon installation, the sharp portions of the electrode wires are forced though the patient's skin. Upon installation a torsional force is also applied to the wires since the bent portion on each wire cannot move within the mating slot on the lower housing. The upper portion 110 is held in position with respect to the lower portion 150 via detent portions 112 and 114 on the upper portion 150 engaging detent portions 170 and 172 on the lower portion respectively. Upon removal the torsional spring force from the wires act such that the raised portions push the upper housing 110 back up and away from the lower housing 150 and the sharp portions of the electrode wires are withdrawn from the patient's skin and back into the cavity between the upper and lower housing.

FIG. 3B shows a portion of electrode assembly 100 while installed in a patient's tissue 190. According to some embodiments, the height of the upper and lower housing during installation is about 0.17 inches. As can be seen, the portions of each of the wires 120 and 130 including the sharp portions 122 and 132 penetrate the patient's skin tissue 190 so as to make a reliable low impedance electrical connection.

Figure 4A:
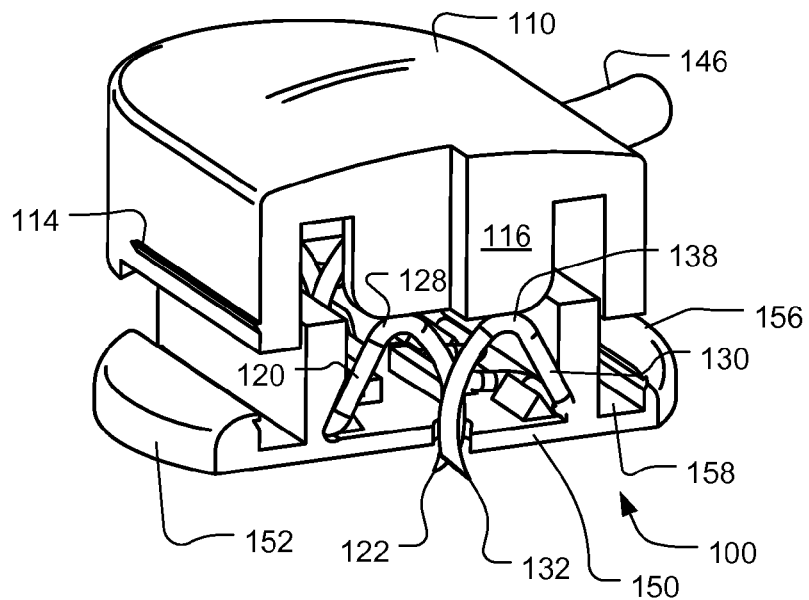
FIGS. 4A-D are cut-away perspective views of an electrode assembly, according to some embodiments.
Figure 4B:
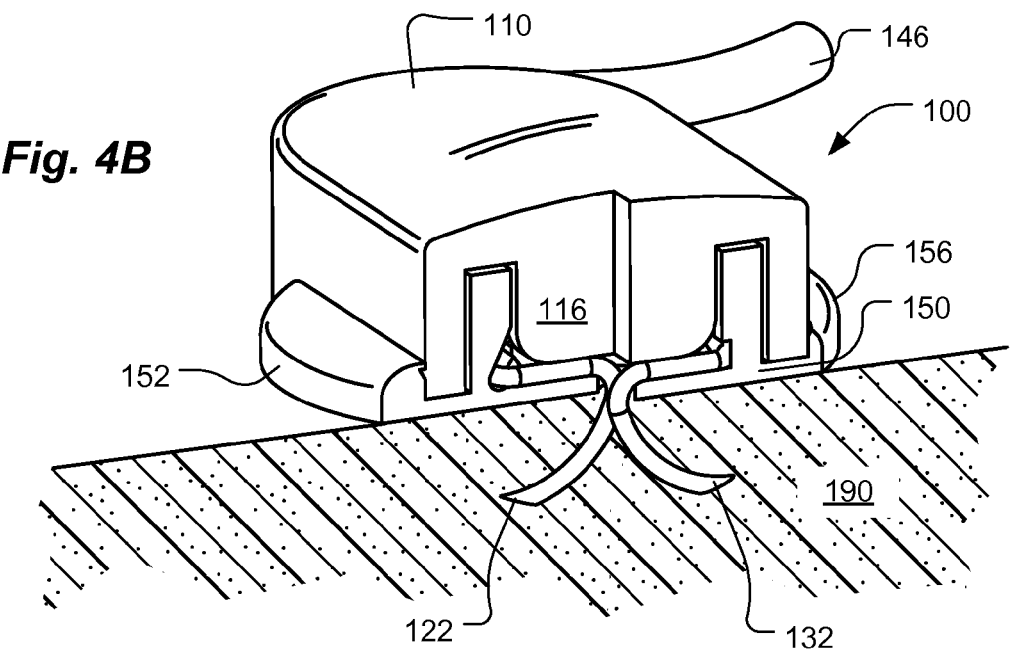

FIGS. 4A-D are cut-away perspective views of an electrode assembly, according to some embodiments. FIG. 4A shows a portion of electrode assembly 100 prior to installation on a patient's tissue. Upper housing 110 is shown having two locking detent portions 112 and 114. Electrode wire 120 has raised portion 128 and a sharp portion 122, and wire 130 has a raised portion 138 and sharp portion 132. The conducting core of electrode wire 146 is electrically connected to a contact plate that is electrical contact with the electrode wires 120 and 130. As can be seen, the raised portions 128 and 138 are engaged by protrusion 116 on the upper housing 110 such that by pressing the upper housing 110 into the lower housing 150 upon installation, the sharp portions of the electrode wires are forced though the patient's skin. FIG. 4B shows a portion of electrode assembly 100 while installed in a patient's tissue 190. Upon installation, a torsional force is also applied to the wires since the bent portion on each wire cannot move within the mating slot on the lower housing. As can be seen, the portions of each of the wires 120 and 130 including the sharp portions 122 and 132 penetrate the patient's skin tissue 190 so as to make a reliable low impedance electrical connection.

Figure 4C:
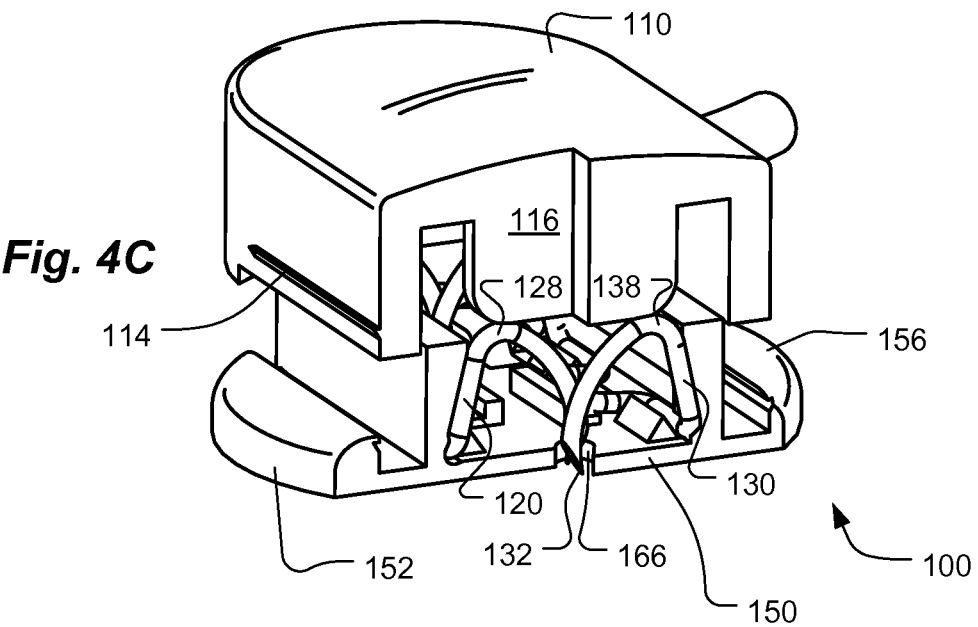
Figure 4D:
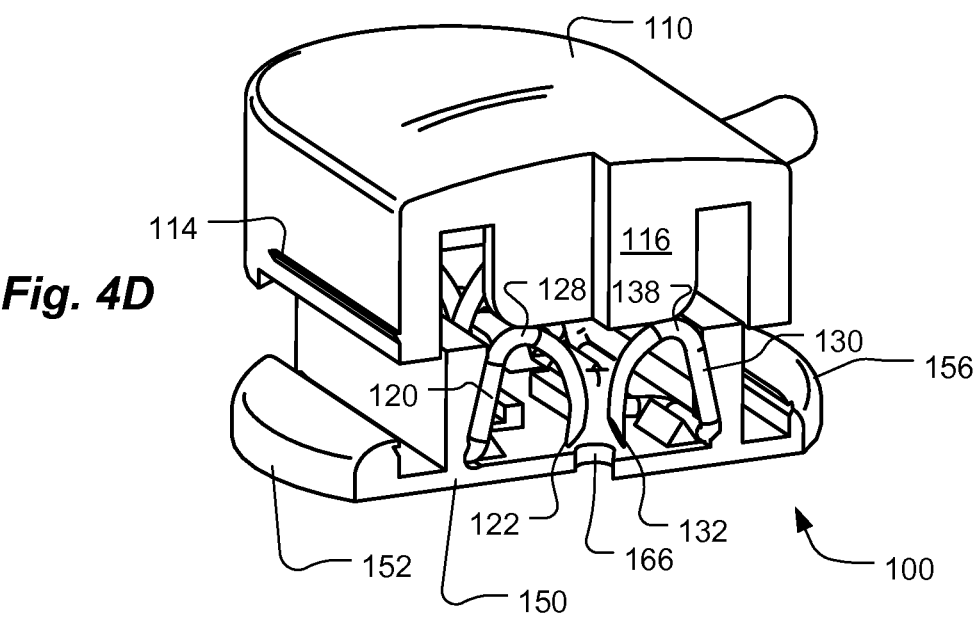

FIGS. 4C and 4D show the electrode assembly 100 after removal from the patient's skin tissue. Upon removal, the torsional spring force from the wires act such that the raised portions 128 and 138 push on protrusion 116 of upper housing 110 so as to push upper housing 110 back up and away from the lower housing 150 and the sharp portions 132 and 122 of the electrode wires are withdrawn from the patient's skin and back into the cavity between the upper and lower housing. In the case of FIG. 4D, the wires 120 and 130 are dimensioned such that upon retraction after removal from the patient's skin tissue, the sharp portions 122 and 132 are completely withdrawn through hole 166 in lower housing 150 and the sharp portions 122 an 132 no longer align with the hole 166. In this way, according to some embodiments, a subsequent accidental pressing of the upper and lower housing together does not force the sharp portions 122 and 132 back through the hole 166.

Figure 5A:
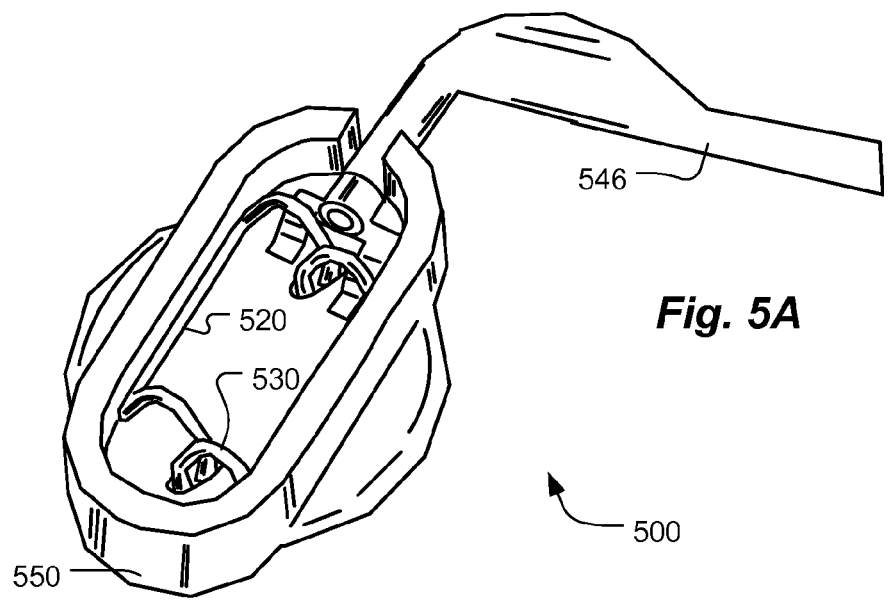
FIGS. 5A-C are perspective views of portions of an electrode assembly, according to some embodiments.
Figure 5B:
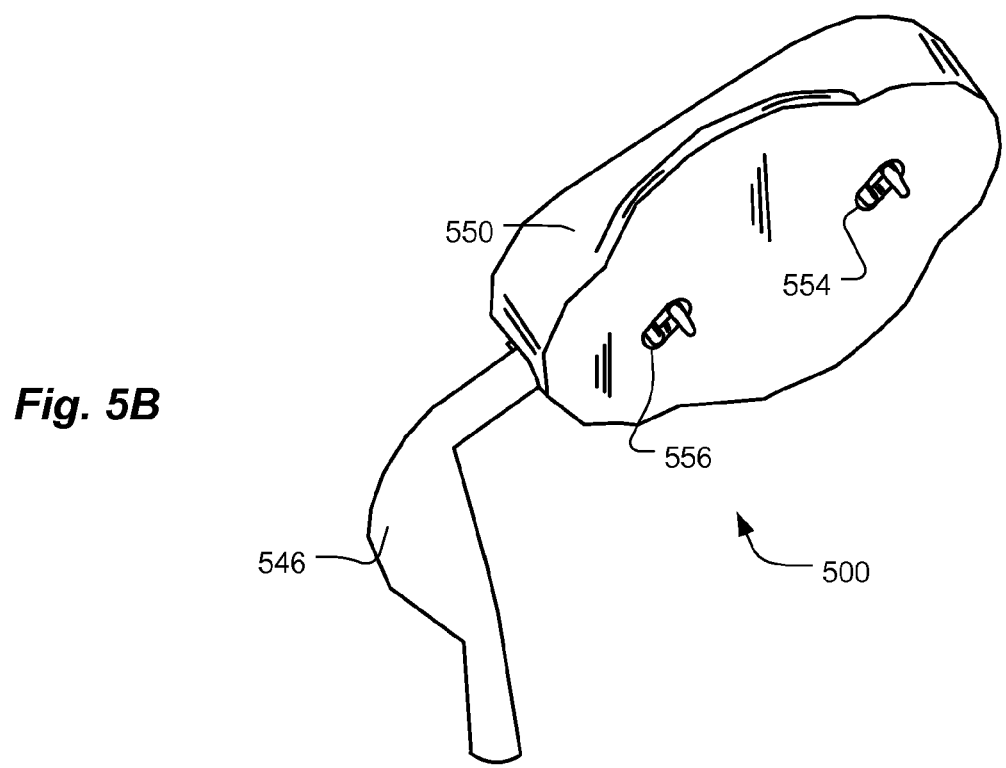
Figure 5C:
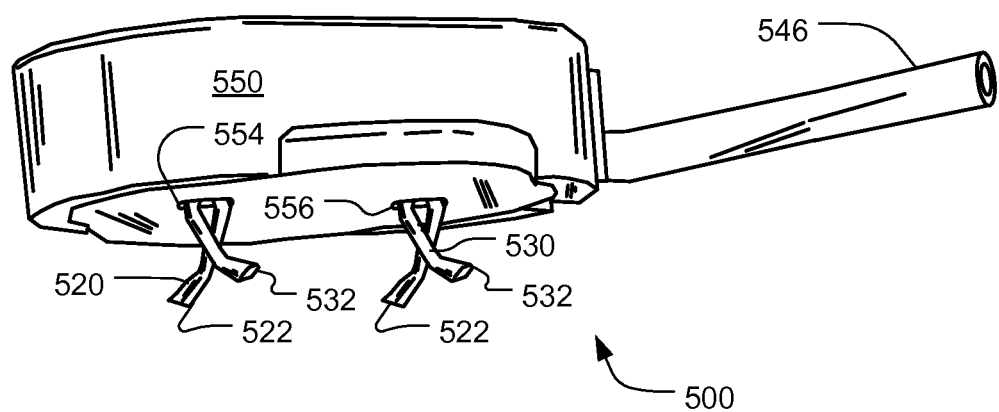

FIGS. 5A-C are perspective views of portions of an electrode assembly, according to some embodiments. An upper housing is not shown so as to increase clarity. Two electrode wires 520 and 530 are shown positioned within the lower housing 550. The assembly 500 also includes a lead wire 546. FIGS. 5A-B illustrate the assembly in pre-deployment position. In FIG. 5B, it can be seen that sharp portions of wires 530 and 520 protrude slightly from holes 554 and 556 in lower housing 550. FIG. 5C illustrates the assembly 500 while deployed on the skin of a patient, which is not shown for clarity. As can be seen the sharp portions 522 and 532 of wires 520 and 530 respectively are deployed via hole 554 in lower housing 550, and sharp portions 524 and 534 of wires 520 and 530 respectively are deployed via hole 556 in lower housing 550.

Figure 6:
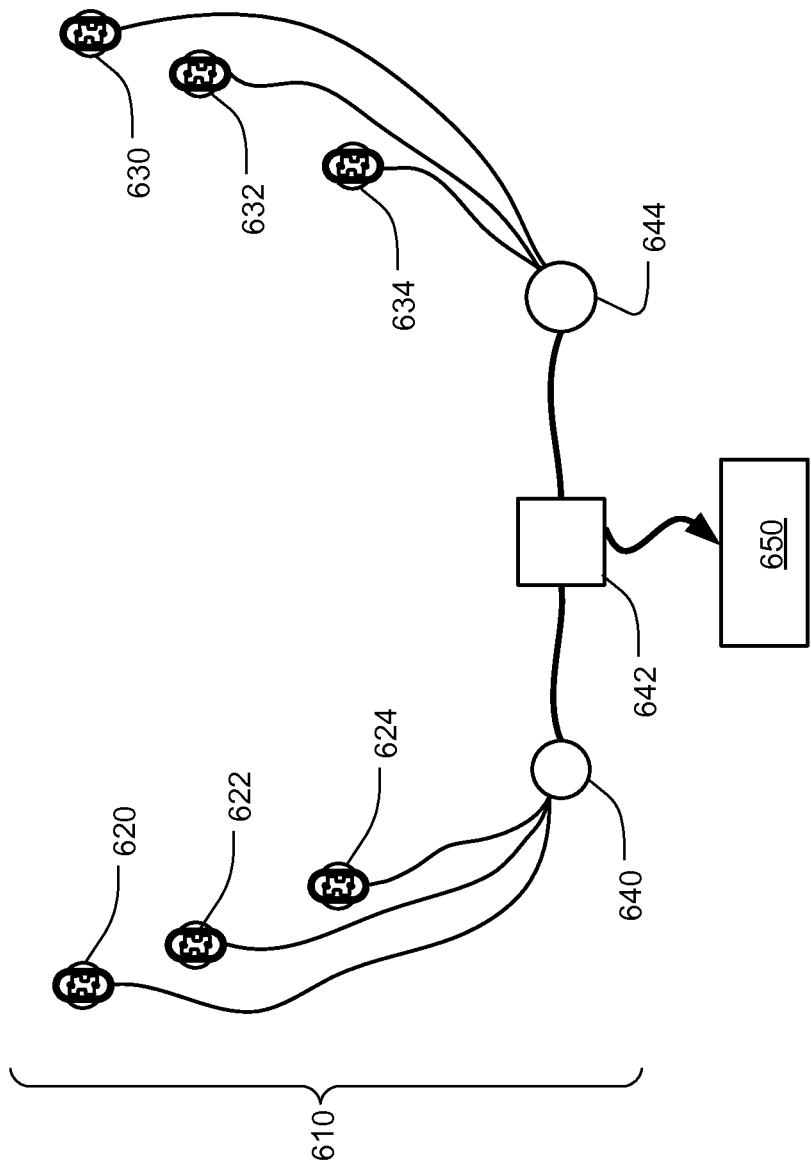
FIG. 6 is a schematic of several transcutaneous electrode assemblies for use in an EEG, according to some embodiments.

FIG. 6 is a schematic of several transcutaneous electrode assemblies for use in an EEG, according to some embodiments. EEG electrode set 610 includes a combination of six safety transcutaneous electrode assemblies which are placed on the scalp and two or more adhesive surface electrodes which are placed on the patients forehead. In particular transcutaneous electrodes 620, 622 and 624 make connections to one side of the patient's scalp, and transcutaneous electrodes 630, 632 and 634 make connections to the other side of the patient's scalp. According to some embodiments, the transcutaneous electrodes 620, 622, 624, 630, 632 and 634 are as shown and described with respect to embodiments of FIGS. 1A-C, 2, 3A-B, 4A-C and/or 5A-C herein. Electrodes 640, 642 and 644 are used to connect to the patient's forehead can be either surface or transcutaneous electrodes, and can be configured in single, multiple or flexible arrays. The conductors are attached to a pre-amp 650 for making EEG measurements.

Figure 7:
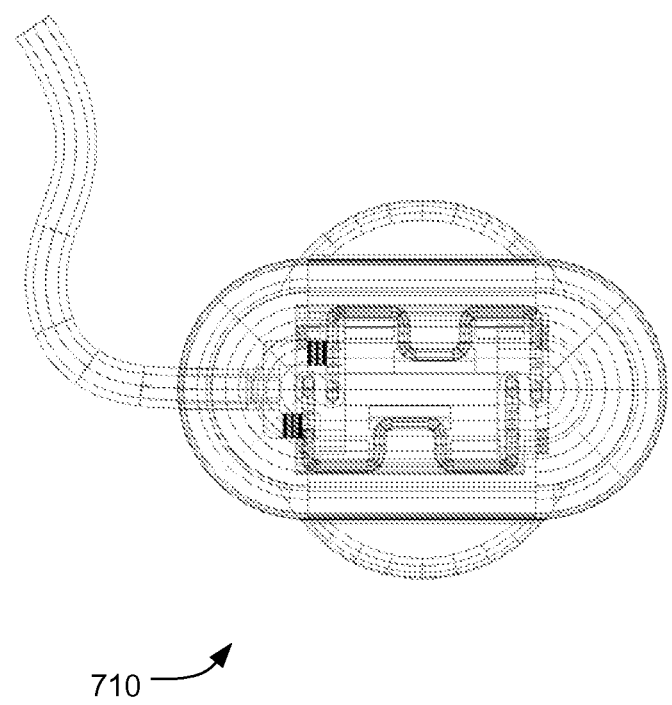
FIG. 7 is a line drawing showing detail of an electrode assembly, according to some embodiments.

FIG. 7 is a line drawing showing detail of an electrode assembly, according to some embodiments. Electrode assembly 710 is shown and the dimensions shown can correspond to one or more embodiments shown and described with respect to FIGS. 1A-C, 2, 3A-B, and 4A-C.

Figure 8A:
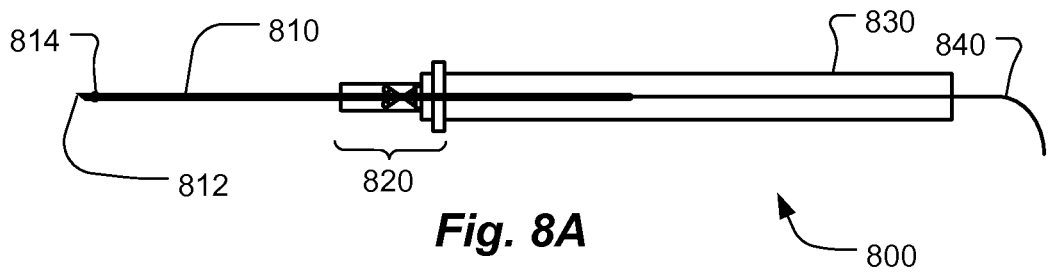
FIGS. 8A-F illustrate a safety electrode assembly according to some embodiments.
Figure 8B:
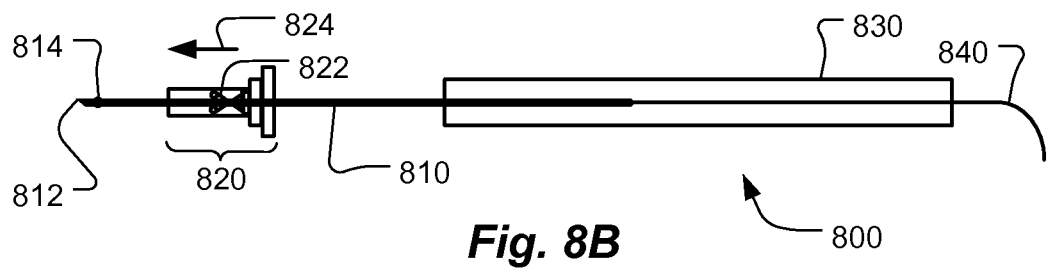
Figure 8C:
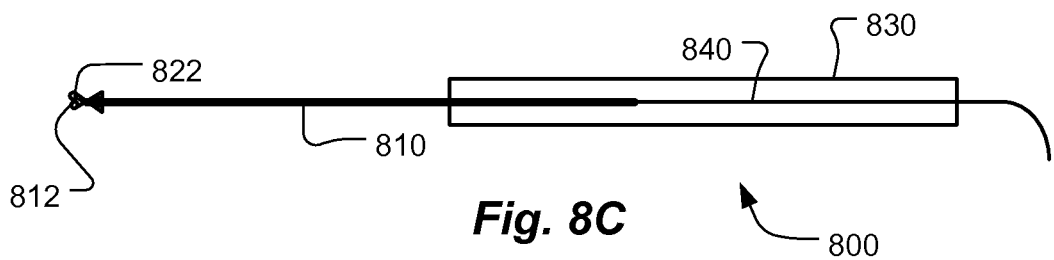
Figure 8D:
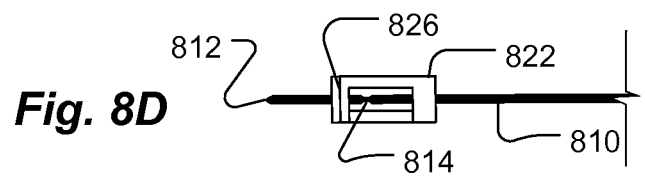
Figure 8E:
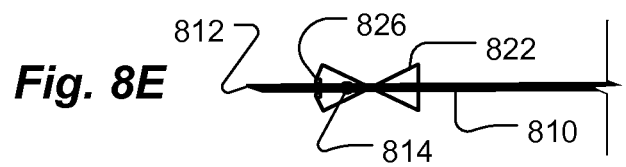
Figure 8F:

FIGS. 8A-F illustrate a safety electrode assembly according to some embodiments. The electrode assembly 800 is a needle type electrode that can be deployed transcutaneously to make a reliable low-impedance connection to a patient's tissue such as skin (subdermal), muscle, nerve, etc. FIG. 8A is a cross section of the assembly 800 prior to or during deployment in the tissue of a patient. The needle 810 has a sharp end 812 and is mostly cylindrical except for a wide portion 814 near the sharp end. The needle 810 is made from conducting material such as a metal and is electrically connected to a lead wire 840. The needle is fixed to a handle body 830 to aid in insertion in and removal from the patient's tissue. The handle body 830 can also be used for stabilizing the needle electrode in the tissue by means of tape or staples. The assembly 800 includes a protective tip 822 that is housed within the tip housing 820 prior to and during deployment of the needle electrode in the patient's tissue. Upon removal of the needle electrode 810 from the patient's tissue, as shown in FIG. 8B, the tip housing 820 is moved forward as indicated by arrow 824. This motion, for example, could be accomplished during removal of the needle from the patient's skin. When the tip housing 820 is moved all the way to the sharp end of needle 810, the protective tip 822 catches on the wide portion 814 such that the end of the protective tip covers and protects personnel from being accidentally injured by the sharp end 812 of needle electrode 810, as shown in FIG. 8C. FIGS. 8D-F show detail of the protective tip 822 and needle electrode 810, according to some embodiments. The tip housing 820 is not shown for clarity. FIGS. 8D and 8E show two side views of the protective tip close to the sharp end 812 of needle 810. According to some embodiments, protective tip 822 is formed of a single piece of metal having curved ends and a small hole that is dimensioned to allow the tip 822 to be slid along the needle 810 but catch on the wide portion 814. The wide portion 814 can be made, for example by deforming the needle material. FIG. 8F shows the protective tip 822 deployed at the sharp end 812 of the needle electrode 810. The tip 822 does not slide along electrode 810 when deployed since it cannot move further towards the tip 812 due to the wide portion 814 and cannot move further towards the handle body due to the tip 812 catching on a folded or rolled over part of the protective tip 822.

Figure 9A:
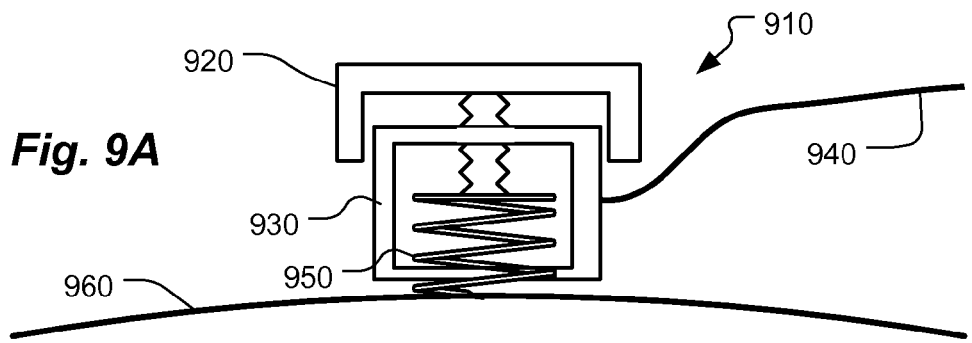
FIGS. 9A-E illustrate a safety electrode assembly according to some embodiments.
Figure 9B:
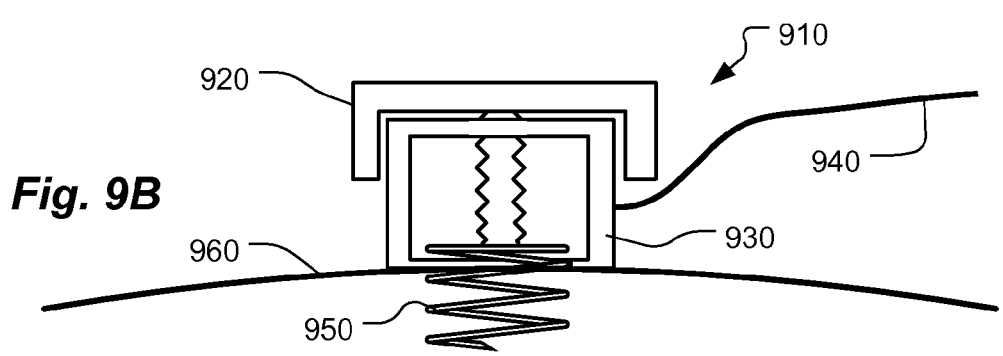
Figure 9C:
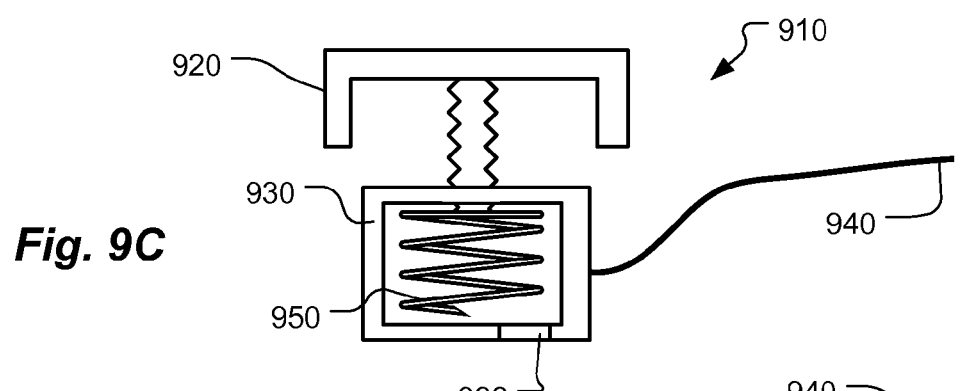
Figure 9D:
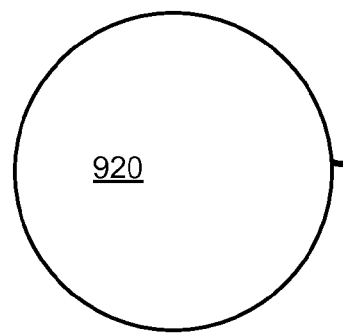
Figure 9E:
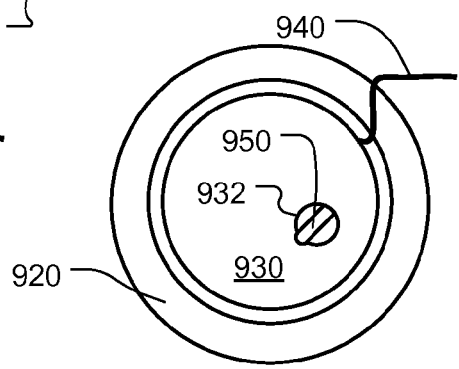

FIGS. 9A-E illustrate a safety electrode assembly according to some embodiments. The corkscrew shaped transcutaneous electrode 950 is sharpened so as to penetrate the patient's skin. The electrode 950 is housed within housing 930 and is electrically connected to conducting lead wire 940. The electrode 950 is applied by holding the assembly 910 against the skin 960 while rotating the upper knob 920. FIG. 9B illustrates the electrode 950 penetrating the skin 960. The electrode is removed by counter rotation of the upper knob 920 to a full stop. Counter rotation draws the electrode 950 out of the patient's skin 960 and back in to the protective housing 930. At full stop, the entire electrode 950 is drawn into the protective housing 930, as shown in FIG. 9C. FIG. 9D is a top view showing the upper knob 920. FIG. 9E is bottom view, showing the protective housing 930 and the electrode aperture 932 through which the electrode passes to engage the patient's skin. According to some embodiments, the housing 930 contains a conducting gel and/or germicidal capsule so as to further reduce impedance and/or reduce risk of infection.

Figure 10A:
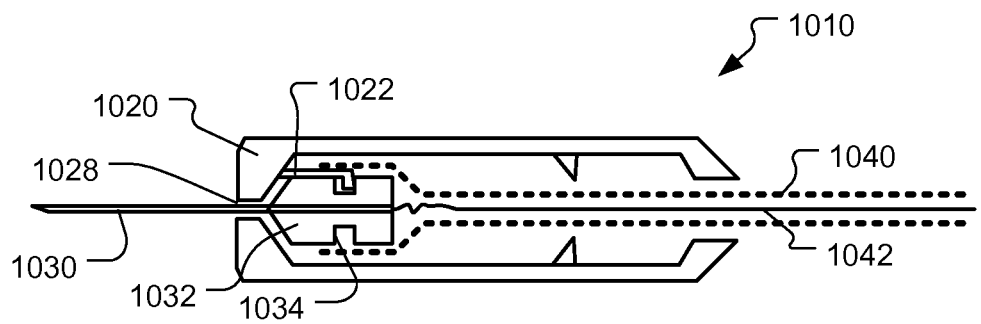
FIGS. 10A-D illustrate a safety electrode assembly according to some embodiments.

FIGS. 10A-D illustrate a safety electrode assembly according to some embodiments. FIG. 10A shows the subdermal electrode assembly 1010 in a position prior to deployment, or during deployment in a patient's skin. A needle electrode 1030 is held by an electrode shuttle assembly 1032. The shuttle 1032 has an annular groove 1034 into which fits a spring retaining clip 1022 and is mounted on handle assembly 1020. Spring clip 1022 is biased to disengage from annular groove 1034 towards that inner wall of handle assembly 1020. Spring clip 1022 is, however, held in place, as shown in FIG. 10A by a shield sleeve 1040 that surrounds the shuttle 1032. Wire lead 1042 is connected to the electrode needle 1030 and has some slack close to the shuttle 1032 as shown. The shield sleeve 1040 also serves as the electrical insulation and protection for wire lead 1042.

Figure 10B:
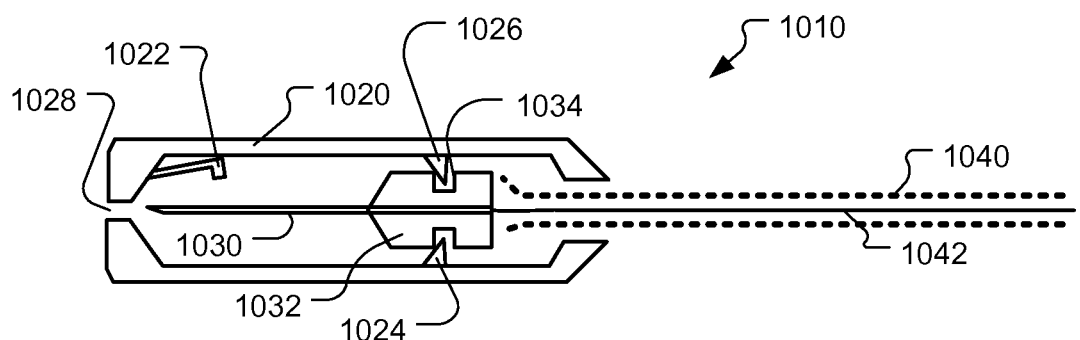
Figure 10C:
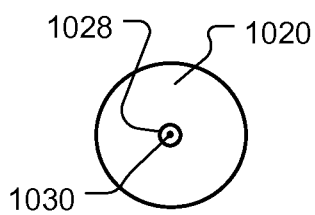
Figure 10D:
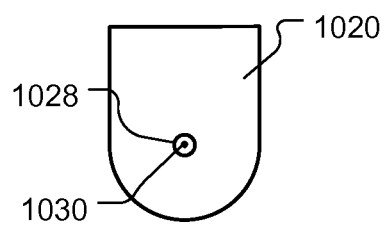

Pulling on the wire lead 1042 and shield sleeve 1040 while holding the handle assembly 1020 will withdraw the shield sleeve 1040 allowing the spring retaining clip 1022 to disengage the groove 1034 on electrode shuttle 1032 permitting withdrawal of the needle electrode 1030 back trough aperture 1028 into a locked position via catches 1024 and 1026 on handle assembly 1020. FIG. 10B shows the needle electrode 1030 safely locked within the handle assembly 1020. FIGS. 10C and 10D show cross-sections of the assembly 1010 according to two different embodiments. The shape shown in FIG. 10D can facilitate stabilization while deployed via tape, for example.

Figure 11A:
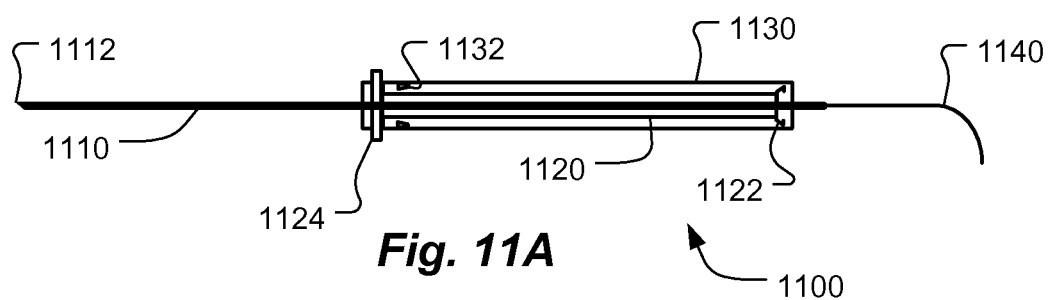
FIGS. 11A-C are cross sections of a safety electrode assembly, according to some embodiments.
Figure 11B:
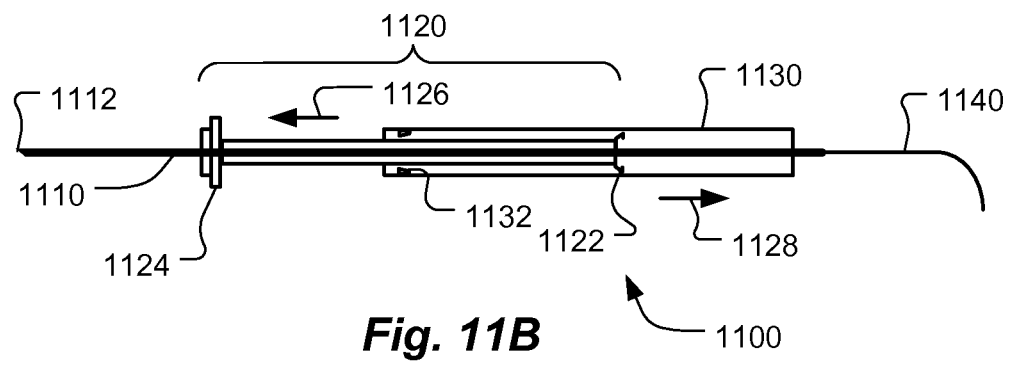
Figure 11C:
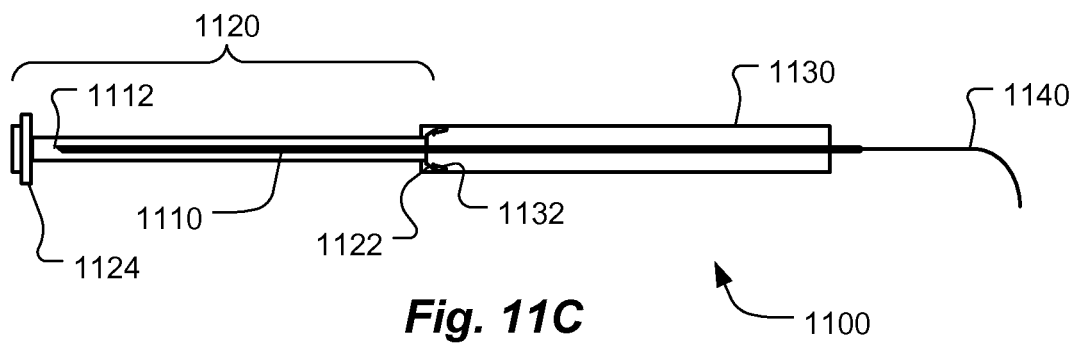

FIGS. 11A-C are cross sections of a safety electrode assembly, according to some embodiments. FIG. 11A is a cross section of the assembly 1100 prior to or during deployment in the tissue of a patient. The needle 1110 has a sharp end 1112 and is made from conducting material such as a metal and is electrically connected to a lead wire 1140. The needle is fixed to a handle body 1130 to aid in insertion in and removal from the patient's tissue. The handle body 1130 can also be used for stabilizing the needle electrode in the tissue by means of tape or staples. The assembly 1100 includes a protective sheath 1120 that is slideably housed within handle body 1130 prior to and during deployment of the needle electrode in the patient's tissue. Upon removal of the needle electrode 1110 from the patient's tissue, as shown in FIG. 11B, the sheath 1120 slides relative to the housing body 1130 as indicated by arrows 1126 and 1128. A cylindrical handle 1124 is provided at the tip end of the sheath 1120 so as to facilitate the sliding action upon removal of the electrode from the patient. The sheath 1120 also includes two spring catches 1122 that are dimensioned so as to catch on annular ramp 1132 fixed to the inner surface of handle body 1130. When the sheath 1120 is moved all the way toward the sharp end of needle 1110, spring catches 1122 engage annular ramp 1132 such that sheath 1120 protects personnel from being accidentally injured by the sharp end 1112 of needle electrode 1110, as shown in FIG. 11C.

Figure 12A:
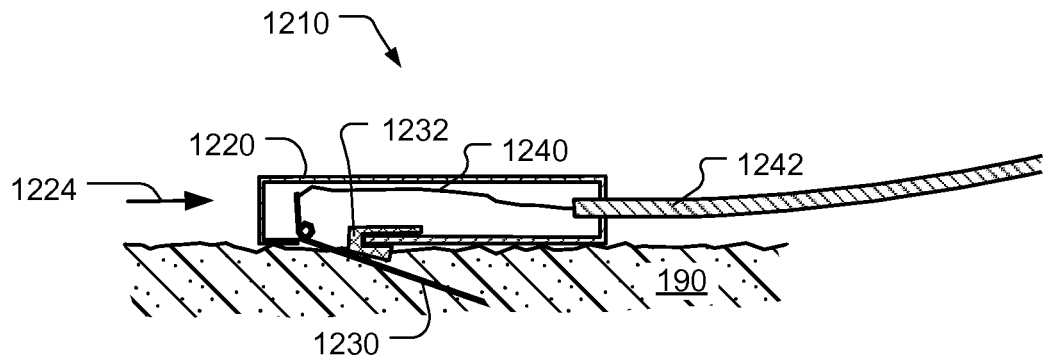
FIGS. 12A-K illustrate a safety electrode assembly according to some embodiments.
Figure 12B:
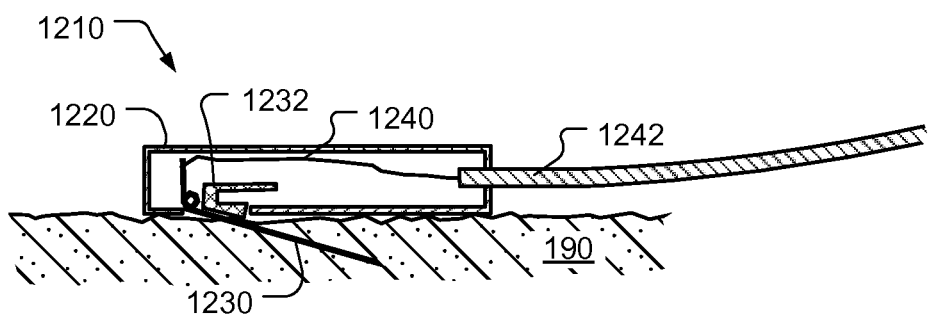
Figure 12C:
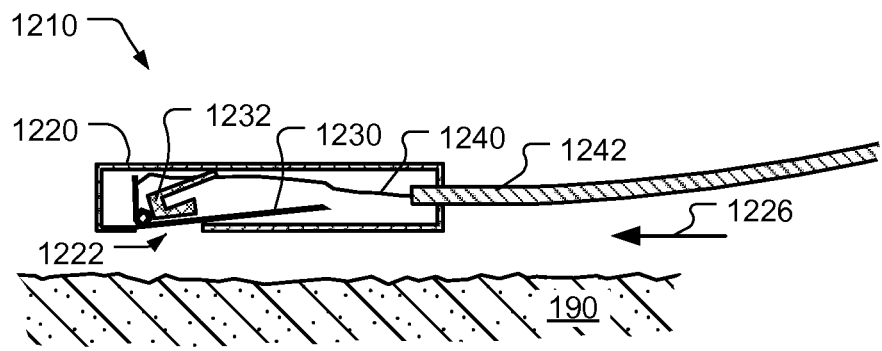

FIGS. 12A-K illustrate a safety electrode assembly according to some embodiments. FIG. 12A shows a subdermal electrode assembly 1210 in the process of being deployed into a patient's skin tissue 190. A movable latch 1232 is positioned as shown and holds needle 1230 in an engaged position as shown. Needle 1230 is mounted within the housing 1220 with a spring force which tends to draw the sharp end of needle 1230 up and into the housing 1220. The arrow 1224 shows the direction of insertion of the electrode relative to the skin tissue 190. The housing 1220 is moved along the skin in the direction of arrow 1224 such that the conducting needle 1230 is driven into the tissue 190. Needle 1230 is attached via conductor 1240 to wire lead 1242. The motion of the electrode assembly 1210 in the direction of arrow 1224 urges latch 1232 to move in the opposite direction relative to the housing 1220. FIG. 12B shows the electrode assembly 1210 fully engaged in tissue 190. Once fully inserted in the skin tissue 190, the latch 1232 is moved by the relative motion against the skin to disengage the housing 1220. FIG. 12C shows the electrode assembly 1210 after removal from the tissue 190. The arrow 1226 indicates the direction of removal of the electrode relative to the skin tissue. On removal the spring loaded needle electrode 1230 springs up into the housing 1220 through a slot in the housing 1220, thus permitting safe handling and disposal by users. Note that the latch 1232 is loosely housed within the housing 1220.

Figure 12D:
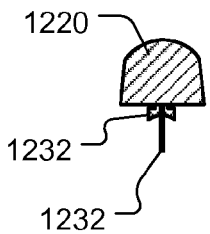
Figure 12E:
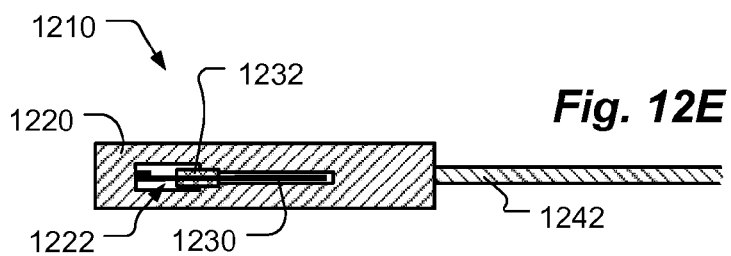
Figure 12F:
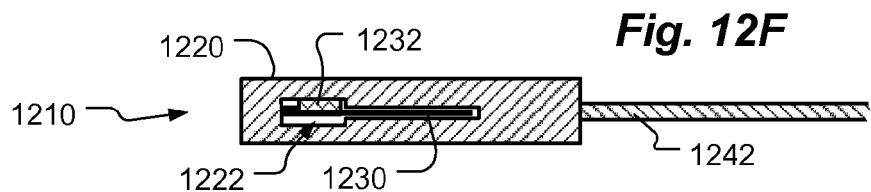
Figure 12G:
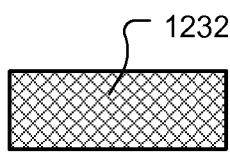
Figure 12J:
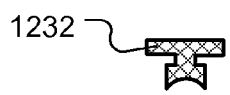
Figure 12H:
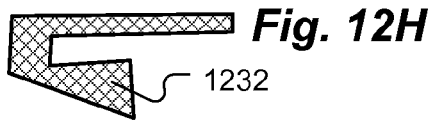
Figure 12K:
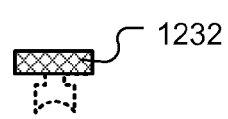
Figure 12I:
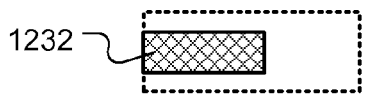

FIG. 12D shows a frontal view of the electrode assembly 1210. FIGS. 12E-F show bottom views of the electrode assembly 1210. In particular, FIG. 12E shows the electrode assembly 1210 with the needle 1230 being held in an engaged position by latch 1232. FIG. 12E is a bottom view of the assembly 1210 prior to or during insertion in a patient's tissue, as shown in FIG. 12A. FIG. 12F is a bottom view of the assembly 1210 after removal from the patient's tissue, corresponding to FIG. 12C. Note the needle 1230 is safely retracted within the housing 1220. FIGS. 12G, 12H, 12I, 12J and 12K are top, side, bottom, front and rear views of the latch 1232, according to some embodiments.

Although many of the embodiments have been described herein with respect to a transcutaneous electrode, according to some embodiments, the same or similar structures are adapted for other transcutaneous uses such as electromyography, electroneurography, botulinum toxin injections, etc.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the inventive body of work is not to be limited to the details given herein, which may be modified within the scope and equivalents of the appended claims.

What is claimed is:

1. A transcutaneous safety electrode assembly comprising:
   a conducting electrode member having a sharp portion dimensioned for penetration of a surface of a skin tissue of a patient; and
   a shielding member that is integrated with said electrode member and is configured for irreversible deployment when removing the sharp portion of the electrode member from the skin tissue of the patent, and configured for permanent shielding of the sharp portion of the electrode member and for permanently preventing accidental injury of personnel from exposure to said sharp portion after it has been deployed for use and removed from the skin tissue of a patient,
   wherein said safety electrode assembly is formed by an upper housing fitting over and movable upwardly and downwardly in a vertical direction with respect to a lower housing, said upper housing being initially coupled to said lower housing by matching detent members on the upper and lower housings in an initial position to be ready for use,
   wherein said conducting electrode is comprised of a wire having a bent portion, a raised portion, and the aforementioned sharp portion, said bent portion being mounted in a fixed position on a lower wall of said lower housing, said raised portion being bent upwardly from the bent portion in contact with an upper wall of said upper housing such that a torsional force is applied on the wire when the upper wall of the upper housing is pressed downwardly toward the lower wall of the lower housing during installation of the sharp portion of the conducting electrode into the skin tissue of a patient, and said sharp portion being positioned proximate a window in the lower wall of the lower housing when the upper and lower housings are in the initial position so that it can be deployed through the window and into the skin tissue of a patient when the upper housing is pressed downwardly on the lower housing to an installation position for installation of the sharp portion into the skin tissue of a patient, and
   wherein said shielding member is formed by withdrawal of the sharp portion of the conducting electrode back through the window and behind the lower wall of the lower housing when the upper housing is released from the installation position on the lower housing for upward movement in the vertical direction to a shielding position, the permanent shielding of the sharp portion of the electrode member being provided by the torsional force of the wire acting to displace the sharp portion from the window when the upper housing is released from contact with the raised portion of the wire in the shielding position.

2. An assembly according to claim 1 further comprising an insulated elongated electrically conducting member in electrical communication with the electrode member.

3. An assembly according to claim 1 wherein the assembly is adapted for transcutaneous placement below the skin surface of the patient.

4. An assembly according to claim 1 wherein the assembly is adapted for intramuscular placement within muscle or nerve tissue of the patient.

5. An assembly according to claim 1 wherein the sharp portion is retracted in to the protective housing at least partially assisted by a spring force so as to at least partially self-retract into the protective housing.

6. An assembly according to claim 5 wherein the spring force is provided at least in part by the electrode member.

7. An assembly according to claim 5 wherein the electrode member is deployed through the skin surface of the patient by a user pressing a button member dimensioned to exert force on the electrode member.

8. An assembly according to claim 7 where the electrode member includes a second sharp portion dimensioned for penetration of the skin surface of a patient.

9. An assembly according to claim 8 wherein the safety electrode assembly remains retained on the skin of the patient when the sharp portion and the second sharp portion of the electrode member are penetrating the skin surface of the patient.

10. An assembly according to claim 9 further including at least one detent dimensioned and positioned to resist movement of the button member during deployment of the electrode sharp portion and second sharp portion penetrating the skin surface of the patient.

11. An assembly according to claim 10 wherein the assembly can be removed from the tissue of the patient by a user pressing at least one portion of the assembly that releases the at least one detent.

12. An assembly according to claim 1 further comprising a second conducting electrode member having a second sharp portion dimensioned for penetration of the skin surface of the patient such that the electrode assembly is able to make bi-polar electrical measurements.

13. A transcutaneous safety electrode assembly comprising:
   a conducting electrode member having a sharp portion dimensioned for penetration of a surface of a skin tissue of a patient; and
   a shielding member that is integrated with said conducting member and is configured for automatic deployment by a single movement of withdrawing the sharp portion of the electrode member from the skin tissue of the patent, and configured for shielding the sharp portion of the electrode member and for preventing accidental injury of personnel by from exposure to said sharp portion after it has been deployed for use and removed from the skin tissue of a patient,
   wherein said safety electrode assembly is formed by an upper housing fitting over and movable upwardly and downwardly in a vertical direction with respect to a lower housing, said upper housing being initially coupled to said lower housing by matching detent members on the upper and lower housings in an initial position to be ready for use,
   wherein said conducting electrode is comprised of a wire having a bent portion, a raised portion, and the aforementioned sharp portion, said bent portion being mounted in a fixed position on a lower wall of said lower housing, said raised portion being bent upwardly from the bent portion in contact with an upper wall of said upper housing such that a torsional force is applied on the wire when the upper wall of the upper housing is pressed downwardly toward the lower wall of the lower housing during installation of the sharp portion of the conducting electrode into the skin tissue of a patient, and said sharp portion being positioned proximate a window in the lower wall of the lower housing when the upper and lower housings are in the initial position so that it can be deployed through the window and into the skin tissue of a patient when the upper housing is pressed downwardly on the lower housing to an installation position for installation of the sharp portion into the skin tissue of a patient, and wherein said shielding member is formed by withdrawal of the sharp portion of the conducting electrode back through the window and behind the lower wall of the lower housing when the upper housing is released from the installation position on the lower housing for upward movement in the vertical direction to a shielding position, the permanent shielding of the sharp portion of the electrode member being provided by the torsional force of the wire acting to displace the sharp portion from the window when the upper housing is released from contact with the raised portion of the wire in the shielding position.

14. An assembly according to claim 13 wherein said conducting electrode and said shielding member are configured for automatic engagement of one or more locking devices by said withdrawal action which permanently prevents accidental injury of personnel by said sharp portion.

* * * * *